(12) United States Patent
Giambattista et al.

(10) Patent No.: US 8,529,510 B2
(45) Date of Patent: Sep. 10, 2013

(54) INJECTION DEVICE

(75) Inventors: Lucio Giambattista, East Hanover, NJ (US); Antonio Bendek, Vernon, NJ (US)

(73) Assignee: SHL Group AB, Nacka Strand (SE)

( * ) Notice: Subject to any disclaimer, the term of this patent is extended or adjusted under 35 U.S.C. 154(b) by 91 days.

(21) Appl. No.: 13/382,915

(22) PCT Filed: Jul. 5, 2010

(86) PCT No.: PCT/SE2010/050770
§ 371 (c)(1),
(2), (4) Date: Jan. 11, 2012

(87) PCT Pub. No.: WO2011/005177
PCT Pub. Date: Jan. 13, 2011

(65) Prior Publication Data
US 2012/0123350 A1   May 17, 2012

(30) Foreign Application Priority Data

Aug. 21, 2009  (SE) ..................... 0950596

(51) Int. Cl.
*A61M 5/20*   (2006.01)
*A61M 5/315*  (2006.01)

(52) U.S. Cl.
USPC ........................ 604/134; 604/220; 604/228

(58) Field of Classification Search
USPC ......... 604/131, 187, 134–139, 198, 207–208, 604/220–223, 228–229
See application file for complete search history.

(56) References Cited

U.S. PATENT DOCUMENTS

| 5,137,516 A | 8/1992 | Rand et al. |
| 2005/0101919 A1* | 5/2005 | Brunnberg .................. 604/197 |

(Continued)

FOREIGN PATENT DOCUMENTS

| WO | 2008/113864 A1 | 9/2008 |
| WO | 2009040607 A1 | 4/2009 |

OTHER PUBLICATIONS

Swedish Patent Office, Intl Search Report in PCT/SE2010/050770, Sep. 23, 2011.

(Continued)

*Primary Examiner* — Nicholas Lucchesi
*Assistant Examiner* — Rebecca E Eisenberg
(74) *Attorney, Agent, or Firm* — Potomac Patent Group PLLC

(57) ABSTRACT

The present invention relates to an injection device comprises a generally elongated tubular housing having opposite proximal and distal ends; a needle shield sleeve slidably and coaxially arranged inside the housing and protruding a distance outside the proximal end of the housing; a syringe carrier mechanism comprising a syringe carrier slidably and coaxially arranged to the needle shield sleeve, wherein said syringe carrier comprises a syringe having a medicament and a needle; a first activator member slidably and coaxially arranged to the housing and connected to said needle shield sleeve; an actuating member slidably and coaxially arranged to the first activator member; a drive mechanism slidably and coaxially arranged to the actuating member and to the syringe carrier mechanism, said drive mechanism being controlled by the actuating member; a second activator member slidably and coaxially arranged to the distal end of the housing and fixedly connected to the actuating member; wherein the first and the second activator members are coaxially movable relative each other from a non-activation position wherein the activator members are abutting to each other to an activation position wherein the activator members are co-acting independent of the sequence in which said activator members are activated; and wherein only in the activation position is the actuating member capable of releasing the drive mechanism to move said syringe carrier mechanism for penetrating the needle and to deliver said medicament though the needle.

8 Claims, 12 Drawing Sheets

(56) References Cited

U.S. PATENT DOCUMENTS

| | | |
|---|---|---|
| 2006/0069351 A9 * | 3/2006 | Safabash et al. .............. 604/136 |
| 2006/0224124 A1 * | 10/2006 | Scherer ......................... 604/220 |
| 2007/0027430 A1 | 2/2007 | Hommann |
| 2010/0331806 A1 * | 12/2010 | Plumptre et al. .............. 604/500 |
| 2012/0209192 A1 * | 8/2012 | Alexandersson ............. 604/135 |

OTHER PUBLICATIONS

Swedish Patent Office, Written Opinion in PCT/SE2010/050770, Sep. 23, 2011.

* cited by examiner

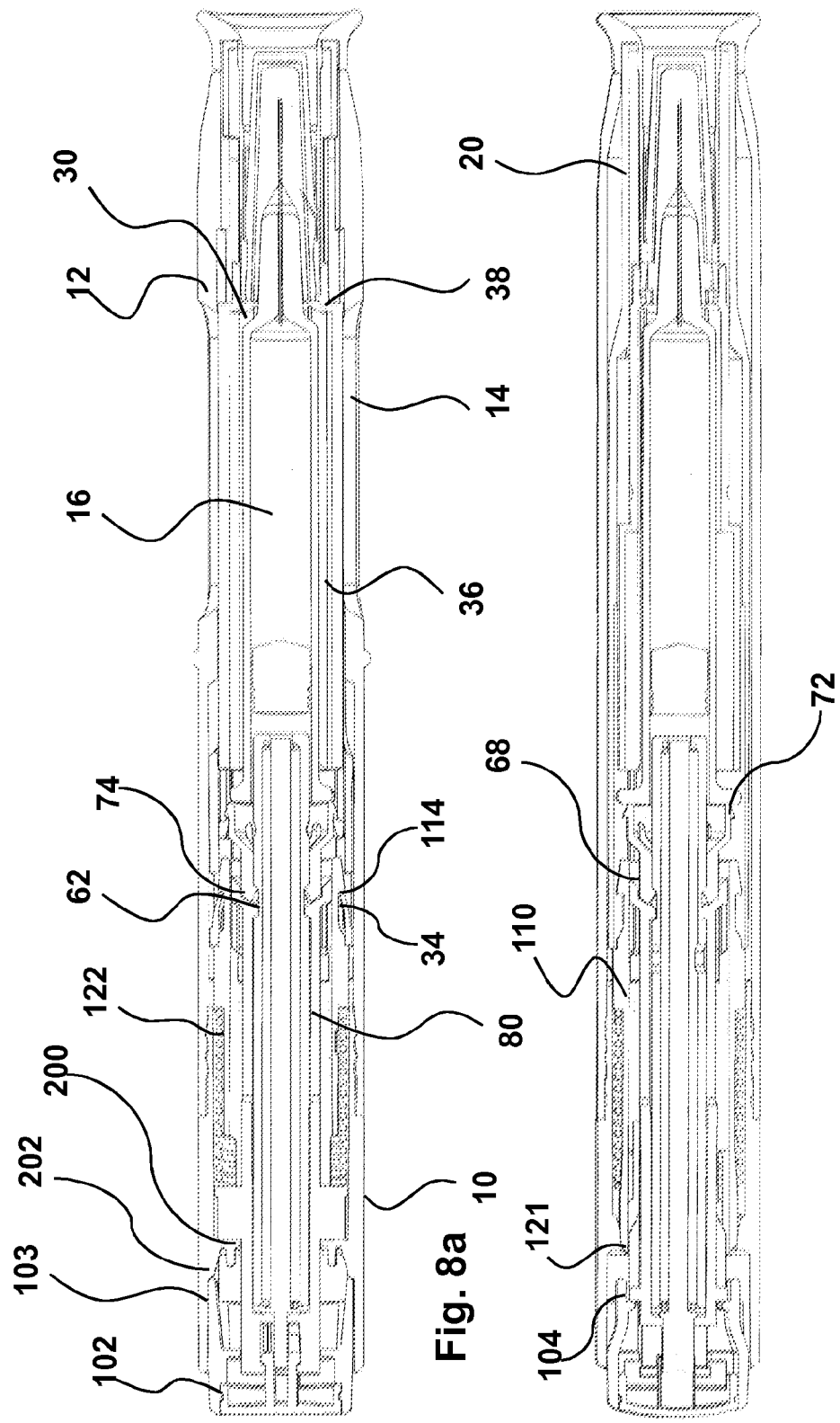

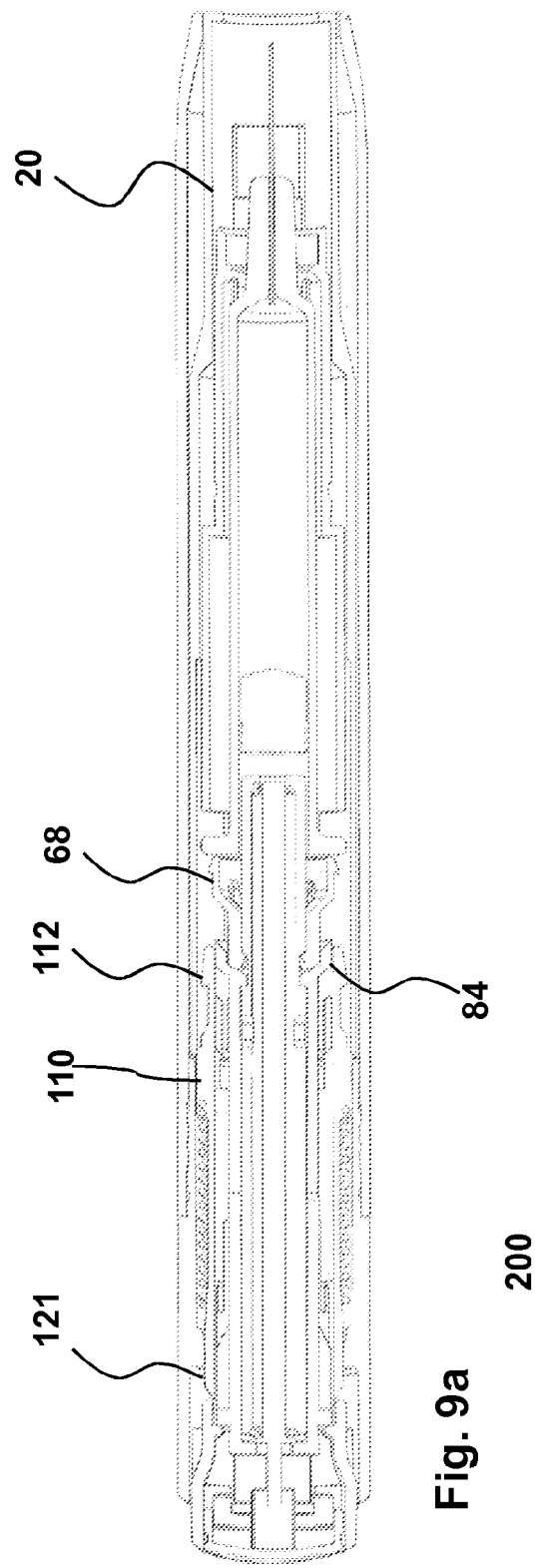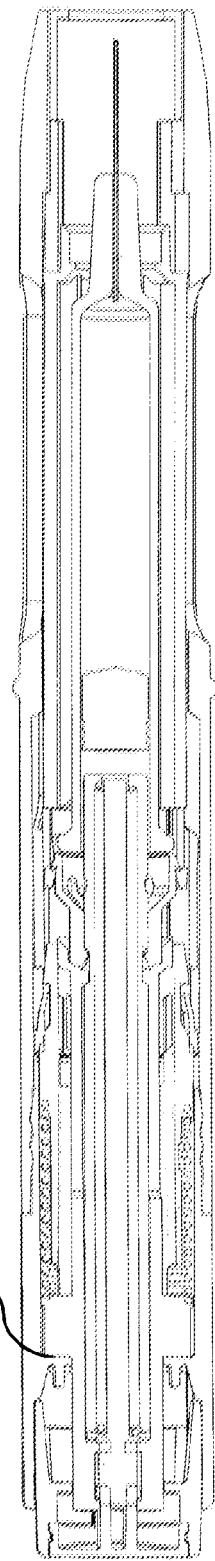
Fig. 9a
Fig. 9b

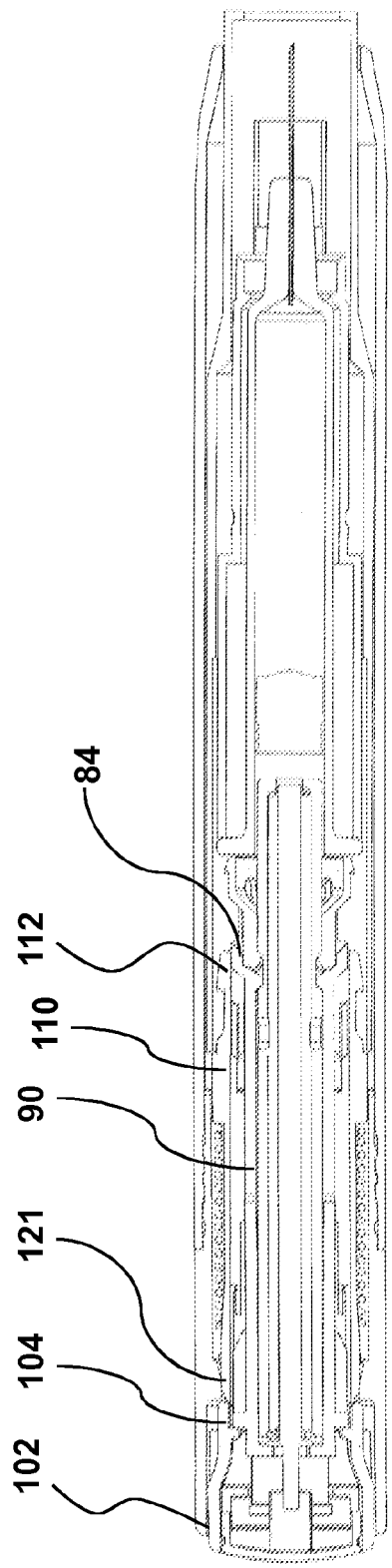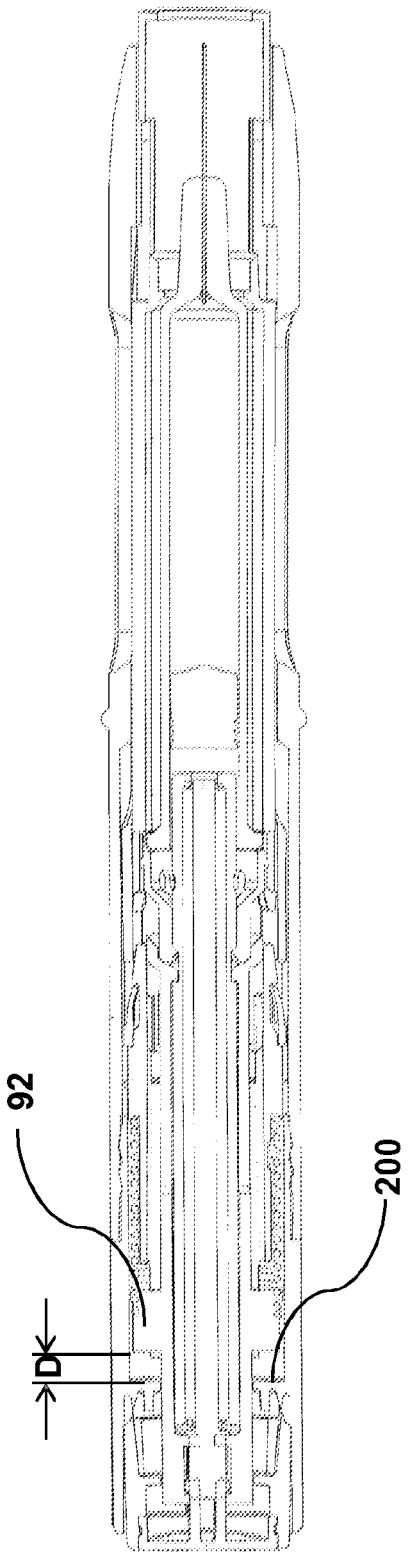
Fig. 10a
Fig. 10b

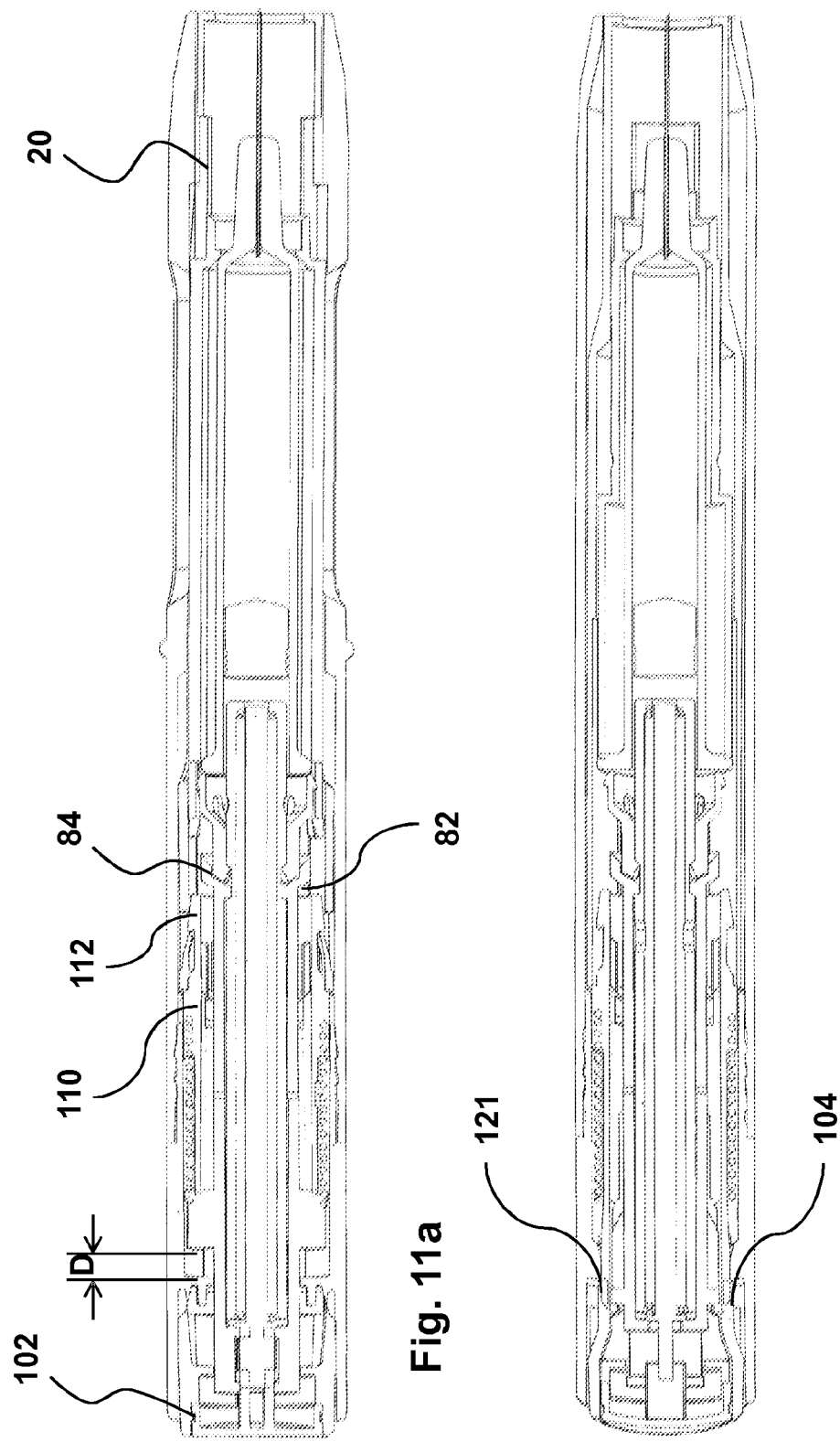

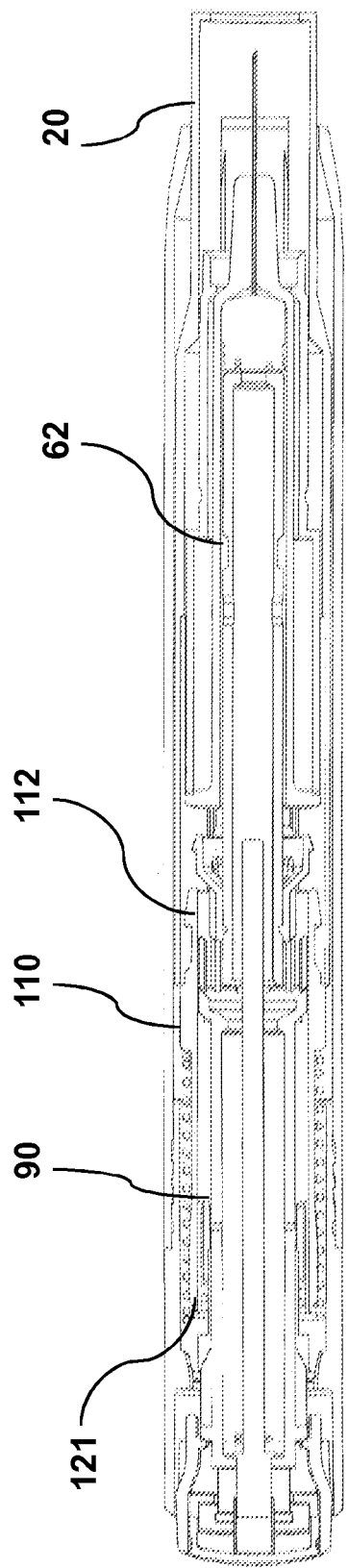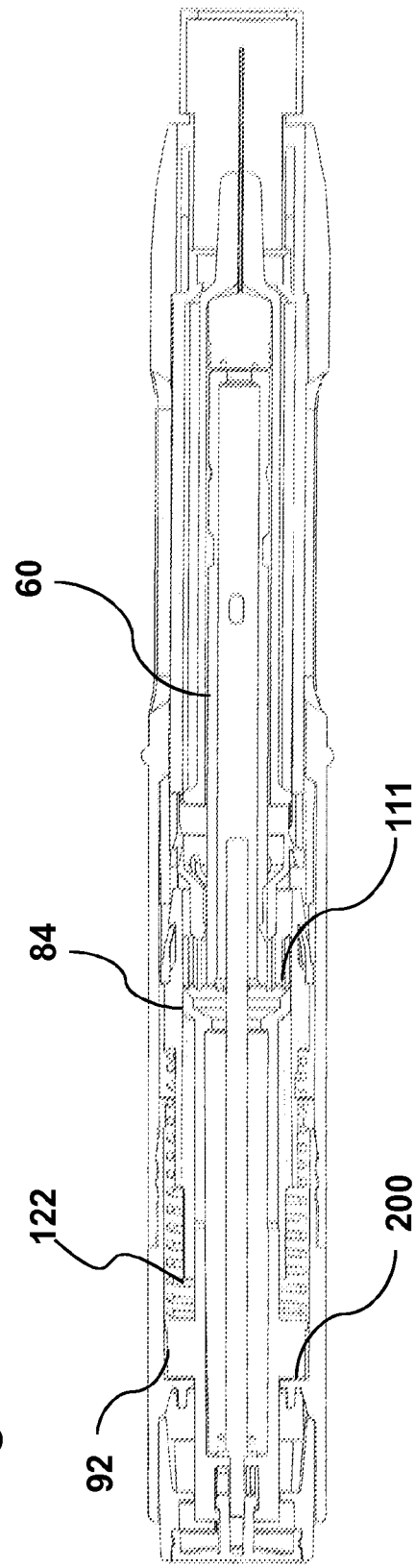
Fig. 12a
Fig. 12b

INJECTION DEVICE

BACKGROUND

The present invention relates to an injection device for administering drugs in a safe and reliable way.

The handling and safety aspects of injection devices, having a certain degree of automatic functions, as well as immediate accessibility in emergency situations are issues that attract a lot of attention when developing this type of device. A few of these devices have safety aspects like a two-step operation before the injection is activated in order to avoid unintended activation, for example if the user comes in contact with the trigger button before the device is placed at an injection site. However many of these solutions are rather bulky and rely also on many components acting or co-operation and in sequence, one trigging another, which may lead to a mal-function, or that the device becomes complicated, hence not user friendly.

One device utilising a high degree of automation is described in International Application Publication WO 02/74774. The device is an auto-injector whereby the injection can be activated by a push button, i.e. penetration and injection, but only when the front end of the injector is pressed against the injection site. It is designed as a kind of two-step operation where the order has to be: pressing the injector at the site and then depressing the button. Any other order of sequence will not result in an activation of the device. This ensures that the injector cannot be accidentally activated by merely pushing the button nor even pushing the button and then pressing the front end.

U.S. Pat. No. 5,137,516 discloses another type of automatically operated injection device. The user first presses the device against the skin in order to move an internal shaft and a sleeve assembly. An actuating button is then depressed, causing a button arm to spread the arms of a retention clip. The separation of these arms releases the head of the plunger rod, which is then moved forwardly under the force of a main coil spring. The plunger rod first moves the entire syringe against the force of a syringe spring. Once the needle has penetrated the skin, the syringe plunger is depressed by the plunger rod, causing the syringe to empty. The main spring of the patented device may be recocked upon reloading of a new syringe assembly. Such reloading is accomplished by a force applied by the syringe piston directly upon the pusher rod of the device.

Even though the above mentioned devices have proved to function well and display a high degree of safety and user-friendliness there is always a desire for improvements of such devices, among them being the design of the mechanism in order to simplify the manufacture and assembly in order to reduce costs but at the same time maintain or even improve the reliability of the function of the device.

SUMMARY

The invention provides an injection device which is uncomplicated and easy to use, which is safe both before, during and after use and which displays a high degree of functionality.

According to one aspect of the invention, an injection device comprises a generally elongated tubular housing having opposite proximal and distal ends; a needle shield sleeve slidably and coaxially arranged inside the housing and protruding a distance outside the proximal end of the housing; a syringe carrier mechanism comprising a syringe carrier slidably and coaxially arranged to the needle shield sleeve, wherein said syringe carrier comprises a syringe having a medicament and a needle; a first activator member slidably and coaxially arranged to the housing and connected to said needle shield sleeve; an actuating member slidaby and coaxially arranged to the first activator member; a drive mechanism slidably and coaxially arranged to the actuating member and to the syringe carrier mechanism, said drive mechanism being controlled by the actuating member; a second activator member slidably and coaxially arranged to the distal end of the housing and fixedly connected to the actuating member; wherein the first and the second activator members are coaxially movable relative each other from a non-activation position wherein the activator members are abutting to each other to an activation position wherein the activator members are co-acting independent of the sequence in which said activator members are activated; and wherein only in the activation position is the actuating member capable of releasing the drive mechanism to move said syringe carrier mechanism for penetrating the needle and to deliver said medicament though the needle.

According to another aspect of the invention, the drive mechanism comprises a plunger rod arranged to act on the syringe and a first compression spring arranged to drive the plunger.

According to a further aspect of the invention, the actuating member comprises flexible tongues having annular inwardly directed ledges, and the plunger rod comprises a circumferential groove having a mutual shape as that of the ledges so that the ledges fit into the groove.

According to yet another aspect of the invention, the plunger is held against a force of the first compression spring by the inwardly directed ledges of the tongues of the actuating member situated in the groove of the plunger rod, and by the first activator member which surrounds and prevents the tongues from moving radial outwards.

According to a further aspect of the invention, the generally elongated tubular housing comprises a distal housing part and a proximal housing part, wherein the distal housing part comprises an annular transversal wall having a through hole which has the shape of the distal part of the actuating member, such that said distal part protrudes distally through said through hole until the distal surface of radial outwardly extending stop ledges of the actuating member abuts against the proximal surface of the annular transversal wall.

According to still another aspect of the invention, the wherein the distal surface of the radial outwardly extending stop ledges of the actuating member is arranged to strike against the proximal surface of the annular transversal wall for giving an audible signal indicating that the delivery has been completed.

The injector comprises a number of radially and axially co-acting means in order to obtain a compact and yet reliable injecting device with rather few components. This implies that the actuating member and the first activating member interact together to hold and lock the drive mechanism radially which is a safe way to lock and store the drive mechanims for long periods until use. As a benefit the user does not have to arm the device before use. When pressing the needle shield sleeve, which in turn is connected to the first activator member, against an injection site, the first activator member axially moves in relation to the actuating member, but not so much that the drive mechanism is released. The step of releasing the drive mechanism is then performed by the second activator member, for example a push button at the distal end of the device, which moves the actuating member axially in relation to the first actuator member until the drive mechanism, is released and thereby the plunger rod is released to act on a stopper within the syringe.

The device is further provided with a second compression spring that urges the needle shield to an extended position surrounding the needle when the needle shield is withdrawn from an injection site after an injection, and a locking mechanism for locking the needle shield in that extended position in order to avoid accidental needle sticks after injection and subsequently after disposal. The device is also provided with an audible signalling mechanism for giving a signal when an injection/delivery has been completed, whereby a remaining force from the first compression spring is used to distally move the actuating member such that a part of it strikes against a part of the housing.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

FIG. 8A is a cross-sectional side view of the embodiment of FIG. 1 in a plane taken 90° in relation to FIG. 1;

FIG. 8B is a cross-sectional side view of the embodiment of FIG. 1;

FIG. 9A is a cross-sectional side view of the embodiment of FIG. 1 when the needle shield has been activated;

FIG. 9B is a cross-sectional side view of the embodiment of FIG. 1 in a plane taken 90° in relation to FIG. 1, when the needle shield has been activated;

FIG. 10A is a cross-sectional side view of the embodiment of FIG. 1, when the push button has been activated;

FIG. 10B is a cross-sectional side view of the embodiment of FIG. 1 in a plane taken 90° in relation to FIG. 1, when the push button has been activated;

FIG. 11A is a cross-sectional side view of the embodiment of FIG. 1 in a plane taken 90° in relation to FIG. 1, when both the needle shield and the push button have been activated;

FIG. 11B is a cross-sectional side view of the embodiment of FIG. 1, when both the needle shield and the push button have been activated;

FIG. 12A is a cross-sectional side view of the embodiment of FIG. 1, after an injection has been performed;

FIG. 12B is a cross-sectional side view of the embodiment of FIG. 1 in a plane taken 90° in relation to FIG. 1, after an injection has been performed;

DETAILED DESCRIPTION

Figure 1:
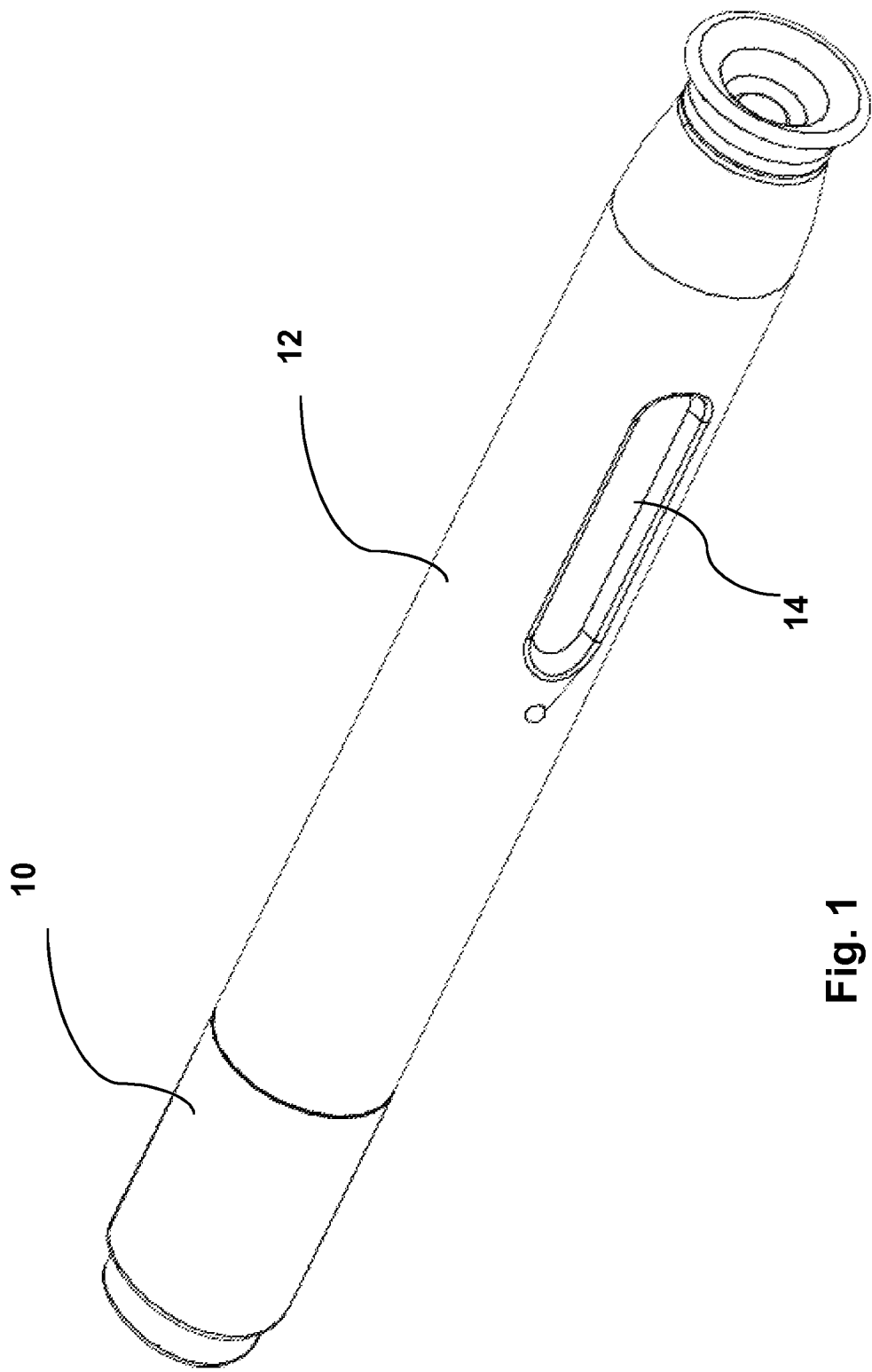
FIG. 1 shows a perspective view of the device comprised in the present invention.

In the present application, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

The embodiment of the present invention shown in the drawings, which is an injection device, comprises:
- a generally elongated tubular housing having opposite proximal and distal ends;
- a needle shield sleeve slidably and coaxially arranged inside the housing and protruding a distance outside the proximal end of the housing;
- a syringe carrier mechanism comprising a syringe carrier slidably and coaxially arranged to the needle shield sleeve, wherein said syringe carrier comprises a syringe having a medicament and a needle;
- a first activator member slidably and coaxially arranged to the housing and connected to said needle shield sleeve;
- an actuating member slidaby and coaxially arranged to the first activator member;
- a drive mechanism slidably and coaxially arranged to the actuating member and to the syringe carrier mechanism, said drive mechanism being controlled by the actuating member;
- a second activator member slidably and coaxially arranged to the distal end of the housing and fixedly connected to the actuating member; wherein the first and the second activator members are coaxially movable relative each other from a non-activation position wherein the activator members are abutting to each other to an activation position wherein the activator members are co-acting independent of the sequence in which said activator members are activated; and wherein only in the activation position is the actuating member capable of releasing the drive mechanism to move said syringe carrier mechanism for penetrating the needle and to deliver said medicament though the needle.

As seen in FIG. 1, the elongated housing comprises a proximal housing part 12 and a distal housing part 10. The proximal housing part 12 is arranged with elongated openings 14 for viewing a syringe 16. The distal end of the proximal housing part is arranged with engagement means as annular recesses e.g. on its inner surface adapted to interface with corresponding engagement means on e.g. the proximal outer surface of the distal proximal part.

Figure 2:
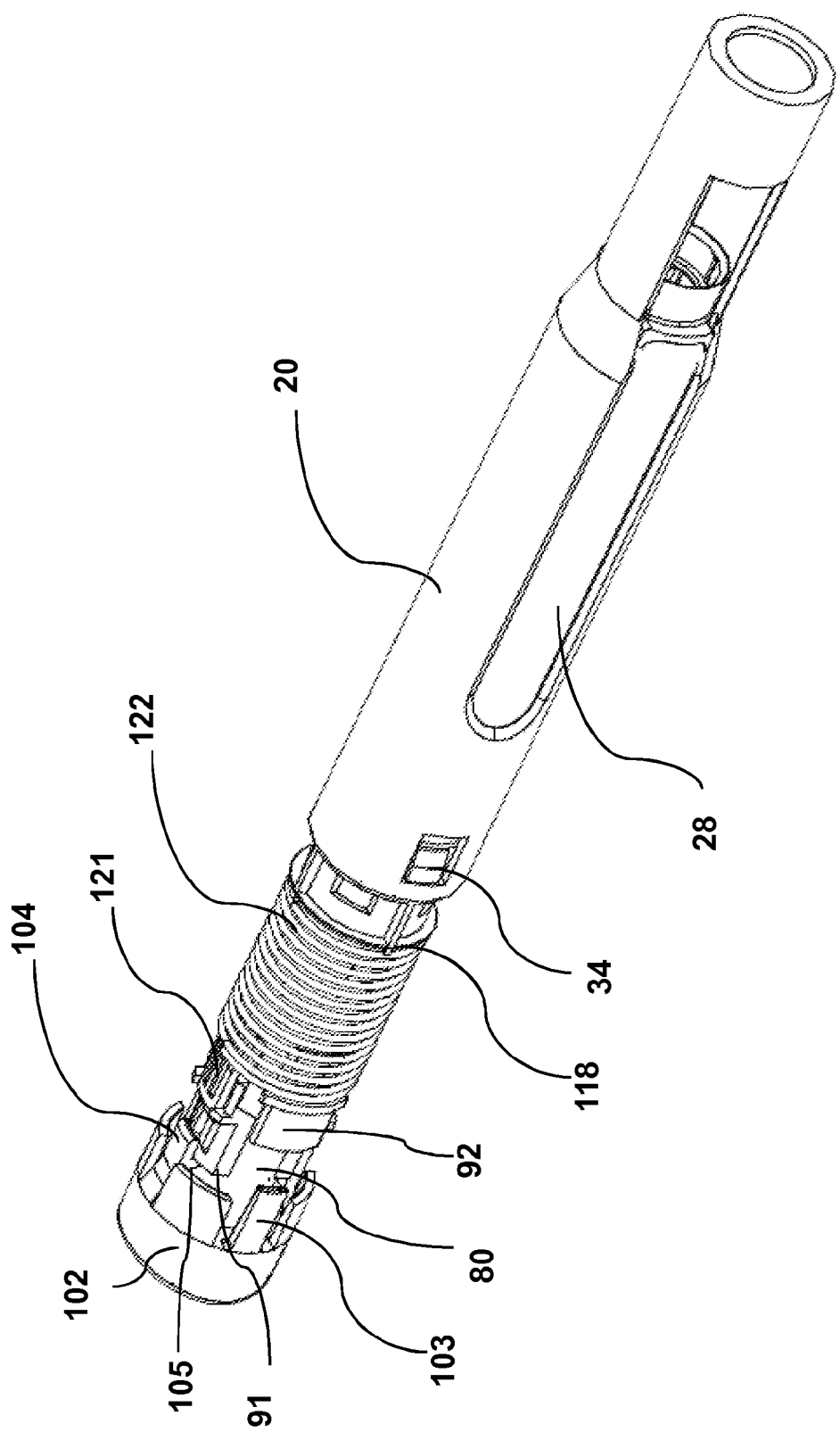
FIG. 2 shows a perspective view of the device without the elongated housing comprised in the present invention.

The needle shield sleeve 20, FIG. 2, hereinafter named needle shield, comprises a first proximal part 22 having a certain diameter and a second distal part 24 having a diameter larger than the proximal part, where these parts are joined by an intermediate conical part 26, FIG. 4. Two elongated grooves 28 are arranged along the needle shield, on opposite sides of the needle shield, also for viewing the syringe, FIG. 2. On the inner surface of the conical part a circumferential ledge 30 is arranged, FIG. 4. At the distal end of the needle shield two openings 32 are arranged opposite each other, where each opening is arranged with somewhat inwardly projecting, flexible, tongues 34, FIG. 4.

Figure 3:
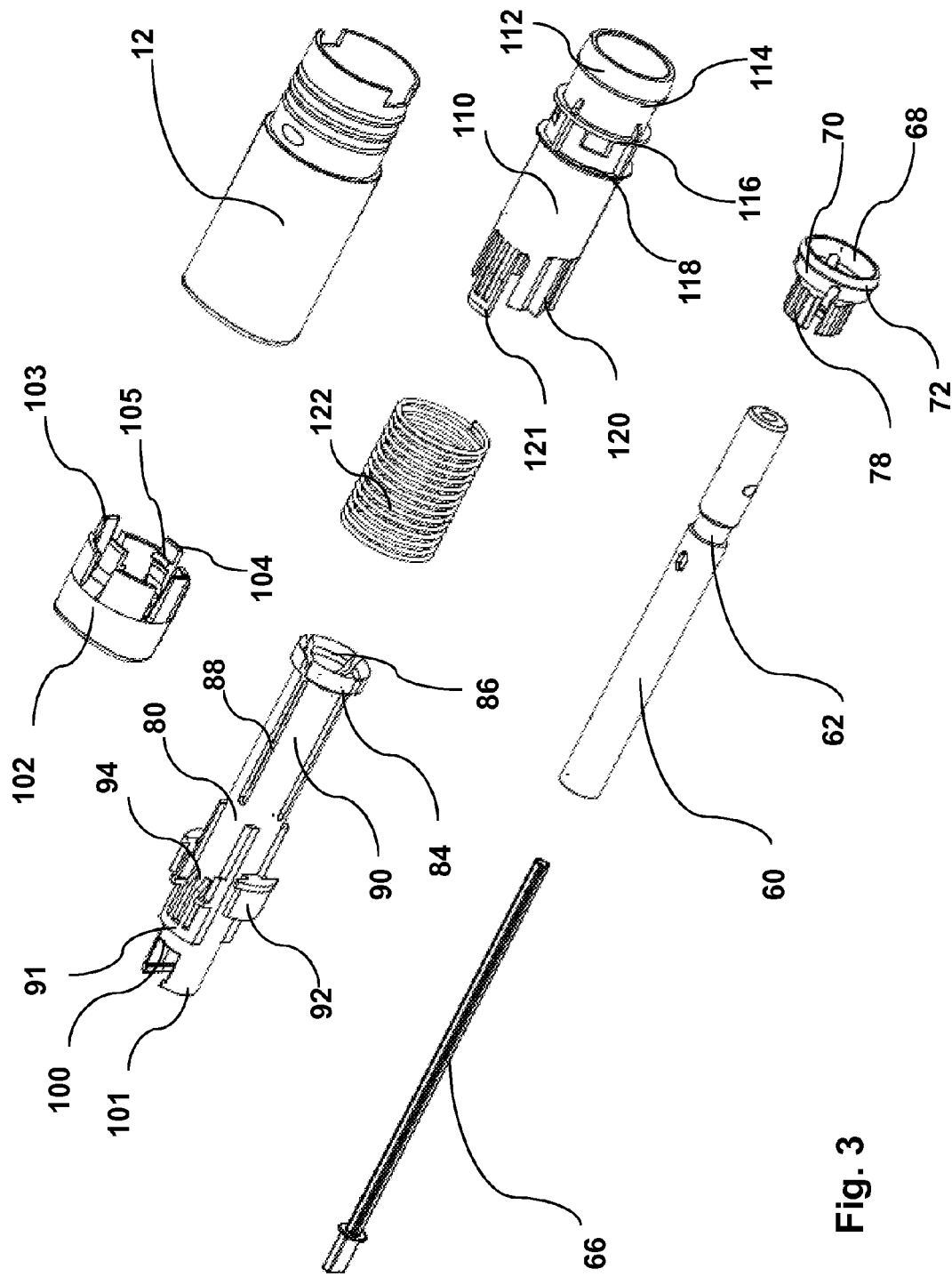
FIG. 3 shows an exploded view of the distal part of the device comprised in the present invention.
Figure 4:
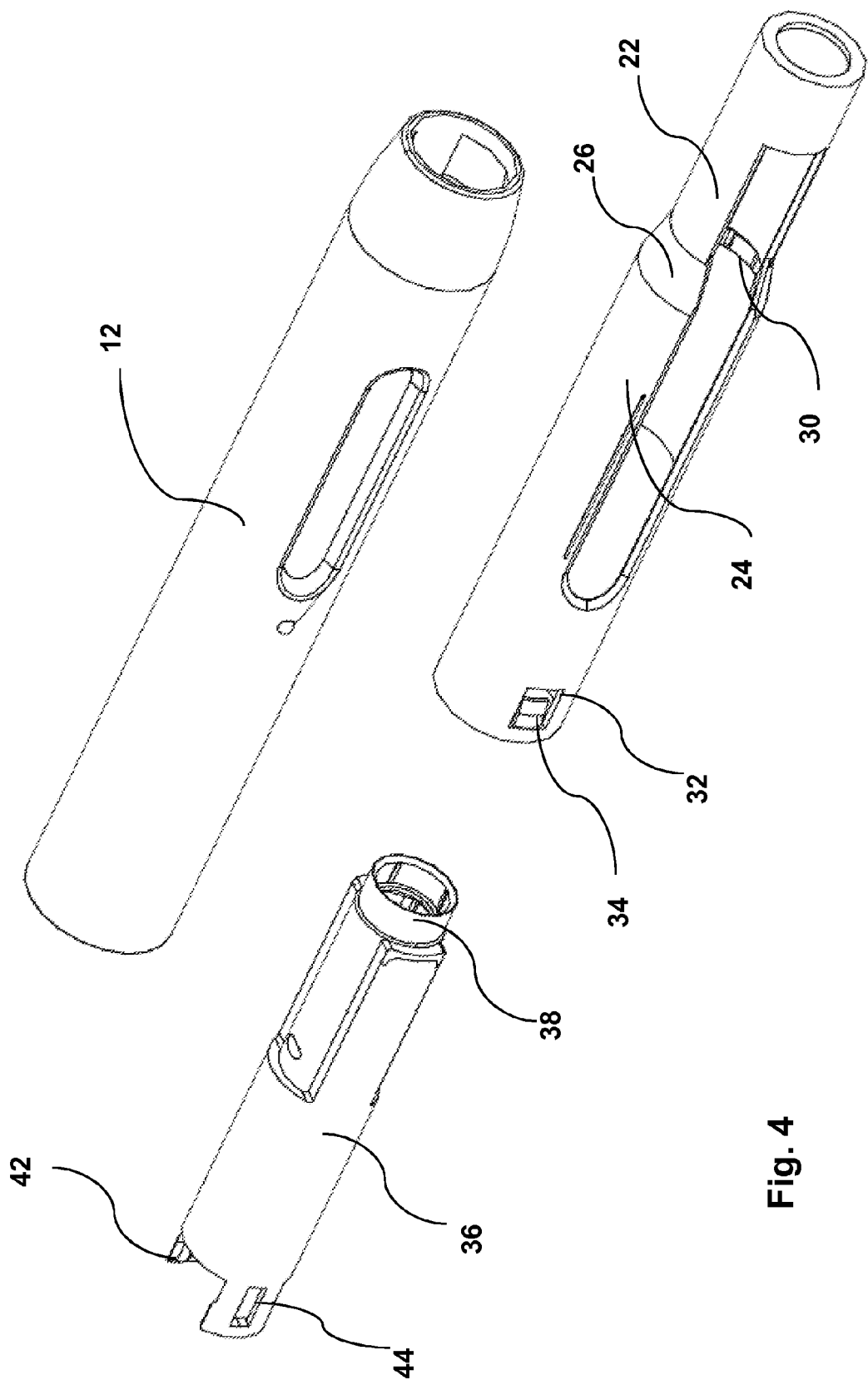
FIG. 4 shows an exploded view of the proximal part of the device comprised in the present invention.

The syringe carrier 36, which is slidably and coaxially arranged inside the needle shield 20 has the form of a general tubular body, FIG. 4. The proximal part of the syringe carrier is arranged with a neck portion 38 of lesser diameter, FIG. 4. Adjacent the neck portion cut-outs have been made on either side to form guide surfaces. These surfaces cooperate with corresponding shapes of the inner surface of the needle shield in order to obtain a stop mechanism against rotation of the syringe carrier relative the needle shield. The distal end of the syringe carrier is arranged with two distally extending tongues 42, where each tongue is arranged with an opening 44 and an inwardly directed ledge on the distal edge of each opening, FIG. 4. The syringe carrier is further arranged with radial inwardly directed flanges on its inner surface in order to obtain a space between the syringe carrier wall and a syringe to be placed inside. The syringe carrier mechanism further comprises a holding member 68, FIG. 3. It comprises a ring-shaped body 70 having an annular ledge 72 arranged around its circumference and a number of flexible tongues 78 directed towards the distal end of the device and wherein each tongue 78 is arranged with radial inwardly directed ledges 74.

The first activator member 110 which is slidably and coaxially arranged to the housing and connected to said needle shield sleeve as it will be described below, has a tubular shaped and comprises a proximal end with a conical part 112 ending in a ledge 114 on its outer surface, FIG. 3. At a distance from the ledge 114, a first annular ring 116 is arranged on the outer surface, FIG. 3. A second annular ring 118 is also arranged a further distance from the ledge 114, FIG. 3. The distal end of the first activator member is arranged with at least two oppositely arranged cut-outs 120 of a generally rectangular shape. Further, the distal end of the first activator member is also arranged with at least two oppositely arranged guide members 121 extending in the distal direction of the device, FIG. 3.

The actuating member 80 which is slidaby and coaxially arranged to the first activator member 110 has a mainly tubular shape. A number of longitudinally directed cut-outs 88 are arranged at the front part of the actuating member so as to form flexible tongues 90, FIG. 3. The proximal end of each flexible tongue 90 has an inclined transition surface 82 which meets with a band-shaped part 84 with enlarged diameter, FIG. 3. On the inner surface adjacent the transition surface 82 an annular inwardly directed ledge 86 is arranged. The actuating member is also provided with two oppositely arranged stop ledges 92 directed radially outwards from the outer surface on either side, where the widths of said stop ledges 92 correspond to the width of the cut-outs 120 of the first activator member, FIG. 3. The actuating member is further provided with at least two oppositely ledges 91 directed radially outwards from the outer surface on either side forming longitudinally extending guide tracks 94, where each guide track is arranged to mate each guide member 121 of the first activator member, FIG. 3. Further, the actuating member is also provided with a transversal distal end wall 100 and with two distally extending engagement means 101.

The drive mechanism which is slidably and coaxially arranged to the actuating member and to the syringe carrier mechanism comprises a plunger rod 60 arranged to act on a stopper of the syringe and a first compression spring (not shown) arranged to drive the plunger rod. The plunger rod 60 is formed as a tube with an outer diameter somewhat smaller than the inner diameter of the syringe body to be used. The plunger 60 is arranged with a circumferential groove 62 with a certain width, wherein the annular inwardly directed ledge 86 of the actuating member 80 and the radial inwardly directed ledges 74 of the holding member fits into, FIG. 3. The first compression spring is arranged to the plunger rod e.g. inside the plunger rod (not shown), and a guide rod 66 is arranged inside the first compression spring, FIG. 3.

The second activator member 102, e.g. a push button, is arranged to be fixedly attached to the distally extending engagement means 101 of the actuating member 80 by corresponding engagement means arranged on the inner surface of a transversal distal wall. Further, the second activator member has a distal portion protruding distally from the distal housing part. The second activator member 102 also comprises two first tongues 104 and at least two second tongues 103 directed towards the proximal direction of the device, where each first tongue 104 has a radial inwardly extending ledge 105, FIG. 3.

The device further comprises a second compression spring 122, hereafter named needle shield spring, coaxially arranged on the first activator member 110. The annular proximal end of the needle shield spring is arranged resting on the second annular ring 118 and the annular distal end of the needle shield spring is arranged resting on the proximal surface of the stop ledges 92 of the actuating member 80, FIG. 2.

Figure 5:
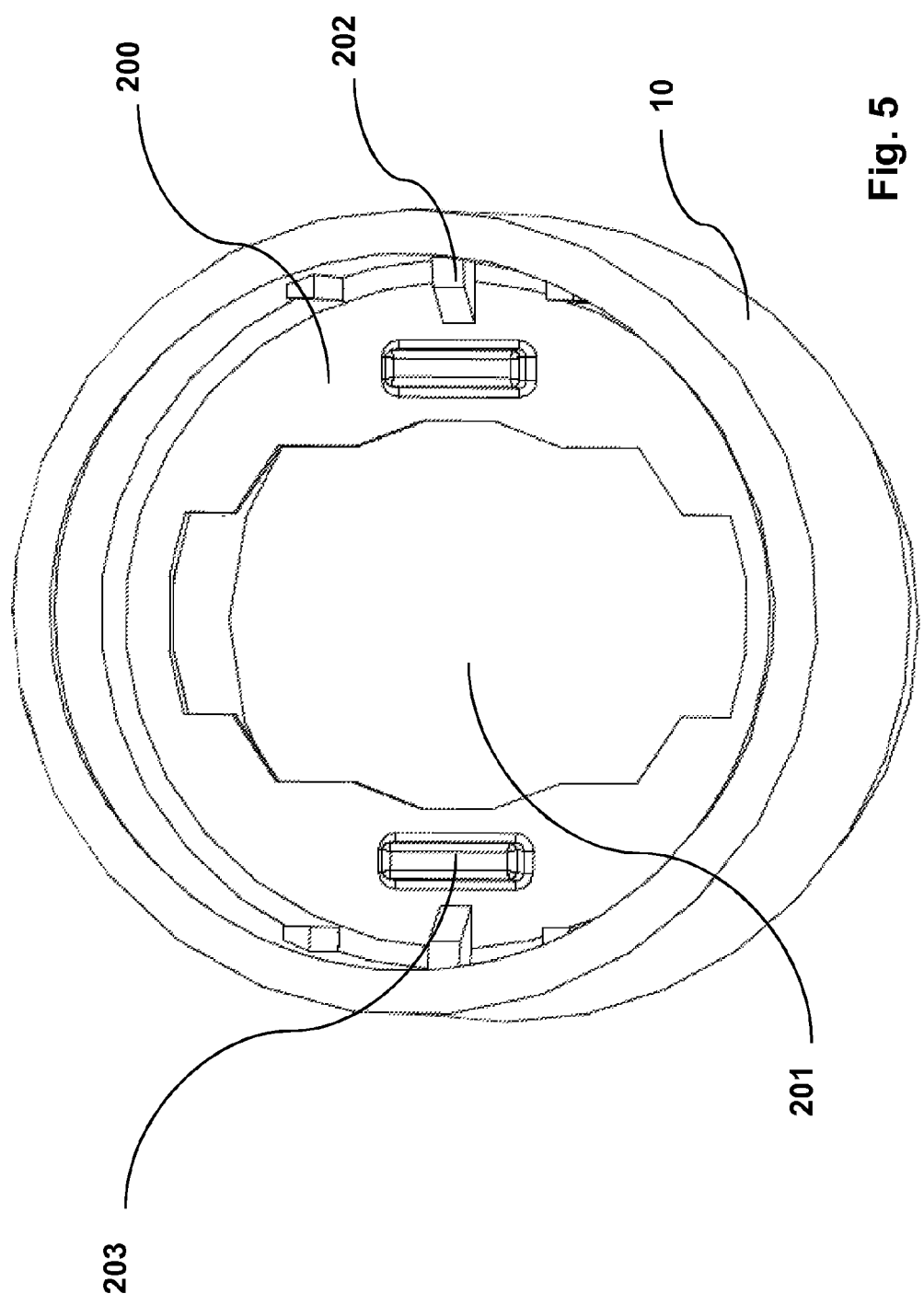
FIG. 5 shows a distal view of the distal housing part of the device comprised in the present invention.

As seen in FIG. 5, the device also comprises interfacing means which are arranged on the inner surface of the distal housing part 10. Said interfacing means comprises an annular transversal wall 200 having a through hole 201 which has the shape of the distal part of the actuating member 80, such that said distal part protrudes distally through said through hole 201 until the distal surface of the stop ledges 92 of the actuating member abuts against the proximal surface of the annular transversal wall 200. The shape of the through hole 201 allows also the guide members 121 of the first activator member to pass through. The interfacing means further comprises at least two distally and longitudinally extending ledges 202 adjacent to the annular distal surface of the transversal wall 200, wherein each ledge comprise an inclination at its distal end. Also, in front of each ledge 202 and at a predetermined distance, a distally extending protrusion 203 protrudes from the distal surface of the annular transversal wall 200.

The function of the device according to the invention will now be described in connection with the FIGS. 6-12

Figure 6:
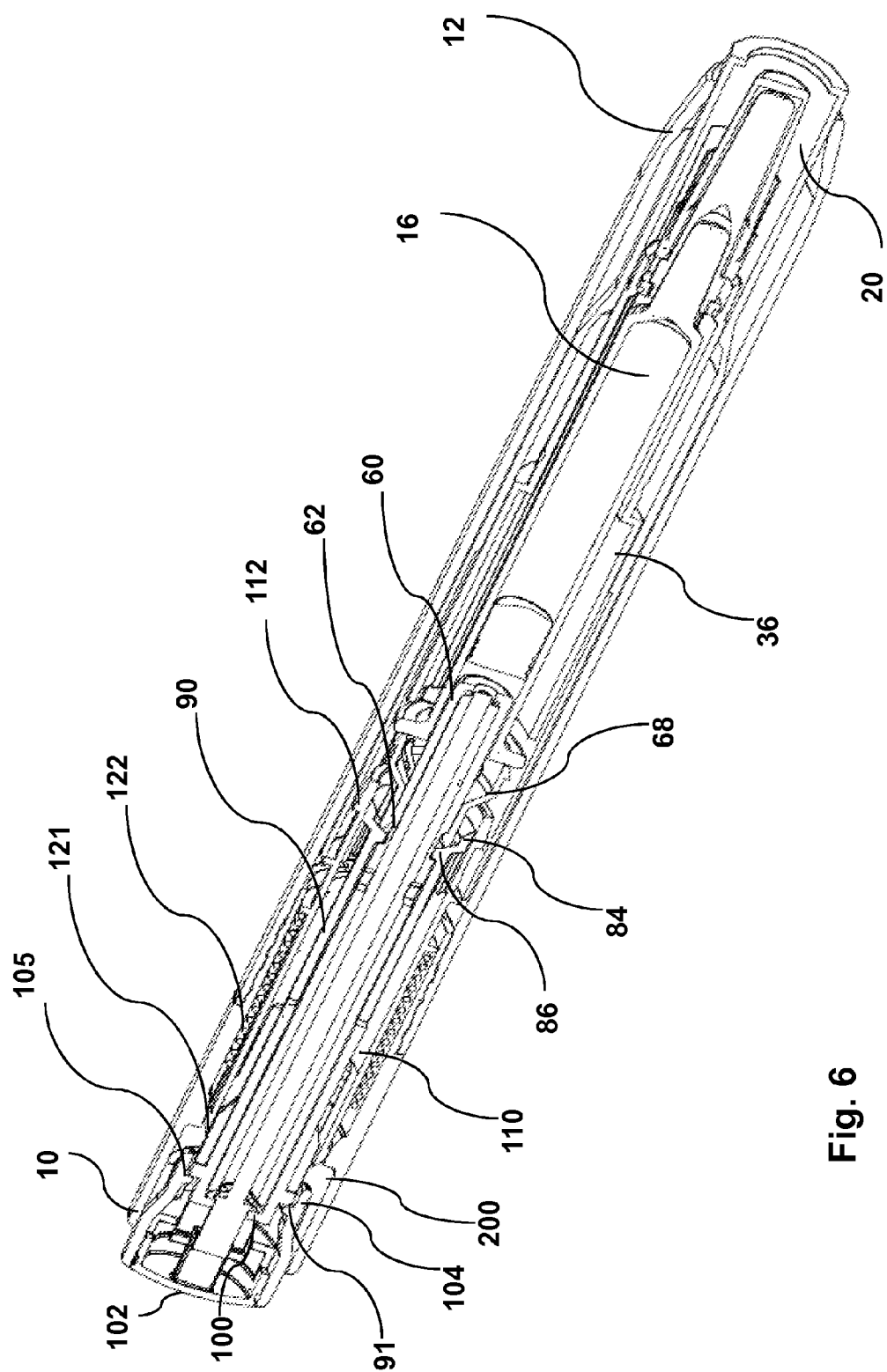
FIG. 6 shows a perspective is a cross-sectional side view of the embodiment of FIG. 1.
Figure 7:
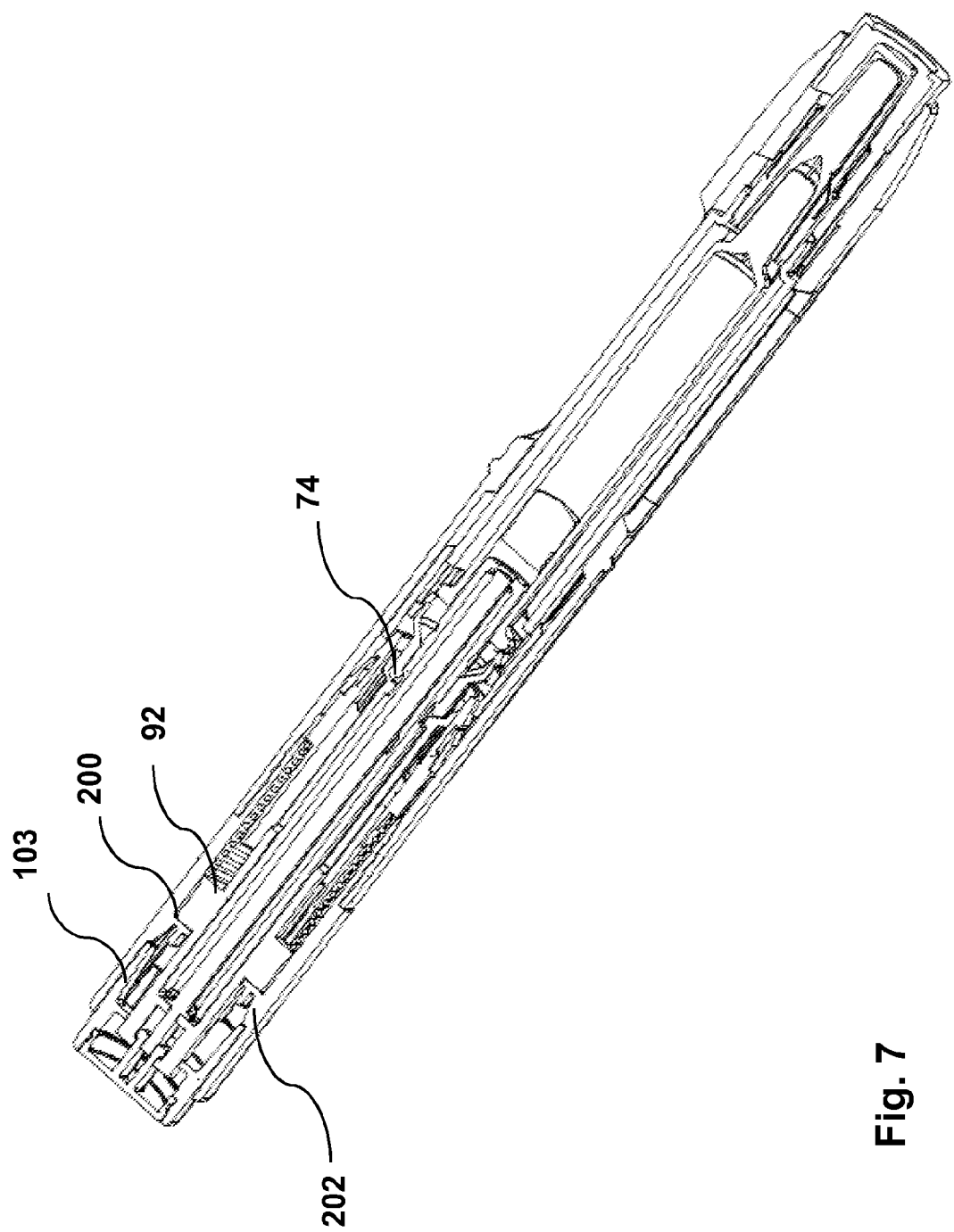
FIG. 7 shows a perspective is a cross-sectional side view of the embodiment of FIG. 1 in a plane taken 90° in relation to FIG. 1.

When the device is assembled and the first and the second activator members are coaxially movable relative each other but in a non-activation position wherein the activator members are abutting to each other, the plunger is held against the force of the first compression spring by the inwardly directed ledges 86 of the tongues 90 of the actuating member 80 situated in the groove 62 of the plunger 60, and by the first activator member 110 which surrounds and prevents the tongues 90 from moving radially outwards, FIG. 6. Further the ledges 74 of the holding member are also arranged in the groove 62, FIG. 7. The syringe 16, the syringe carrier 36, and the needle shield 20 are coaxially placed in the proximal housing part, such that a portion of the front end of the needle shield projects proximally through the front end of the proximal housing part, FIG. 6; and the distal housing part is fixedly attached to proximal housing part by the engagement means forming the elongated tubular housing. The inwardly directed ledges on the distal edge of each opening 44 of the syringe carrier 36 pass the distal end surface of the annular ledge 72 of the holding member 68, and at the same time the tongues 34 of the needle shield 20 fit the distal surface of the ledge 114 of the first activator member 110, FIGS. 8a and 8b. Each radial inwardly extending ledge 105 of the second activator member 102 abuts the ledges 91 of the actuating member 80 and the proximal end of each first tongue 104 of the second activator member 102 abuts each inclined surface of the guide members 121 of the first activator member 110, FIG. 6. Further, the proximal surface of each second tongue 103 of the second activator member 102 faces the inclined surfaces of each longitudinally extending ledge 202 on the inner surface of the distal housing part and adjacent to the annular distal surface of the transversal wall 200, FIG. 8a.

The first and the second activator members are arranged to co-act independent of the sequence in which said activator members are activated as it will be explained below.

The first activator member is firstly activated and the second activator member is subsequently activated.

When the projecting front end portion of the needle shield is firstly pushed distally into the proximal housing part, FIGS. 9a and 9b, against the force of the second compression spring 122, the distal end of the needle shield is in contact with the first annular ring 116 of the first activator member 110 and its movement causes the first activator member to move distally, whereby each guide member 121 of the first activator member 110 comes under the proximal end of each first tongue 104 of the second activator member 102 and a portion of the band-shaped part 84 comes out from the surrounding of the first activator member 110, FIG. 9a. Should the user however remove the injector from the injecting site, before pressing the second activator member, the compression spring 122 will push the actuator sleeve 110 and thereby the needle shield 20 back to its original position.

The second activator member is firstly activated and the first activator member is subsequently activated.

When the second activator member is pushed proximally, FIGS. 10a and 10b, each first tongue 104 of the second activator member 102 comes over each guide member 121 of the first activator member 110. The actuating member is also proximally moved a distance "D" whereby a portion of the band-shaped part 84 comes out from the surrounding of the first activator member 110, FIG. 10b. Should the user however release the second activator member, before pressing the needle shield against the injection site, the resiliency of the second tongues 103 of the second activator member 102 acting on the inclined surfaces of each longitudinally extending ledge 202 on the inner surface of the distal housing part will push the second activator member back to its original position.

Now, when the first and the second activator members are coaxially movable relative each other from a non-activation position wherein the activator members are abutting to each other to an activation position wherein the activator members are co-acting independent of the sequence in which said activator members are activated; and wherein only in the activation position is the actuating member capable of releasing the drive mechanism to move said syringe carrier mechanism for penetrating the needle and to deliver said medicament though the needle, will be explained as below.

When the second activator member is proximally pressed either firstly before subsequently pressing the needle shield against an injection site or subsequently after having pressed the needle cover against an injection site as described above, this causes the actuating member to be proximally moved the distance "D" whereby the band-shaped part 84 of the actuating member 80 comes completely out from the surrounding of the first activator member 110 and the resilient properties of the tongues 90 of the actuating means allows the proximal end of the tongues 90 to flex radially outwards, causing the ledges 86 to move out of the groove 62 of the plunger rod, which then is free to move proximally due to a force of the compressed first compression spring, FIGS. 11a and 11b. The inclined transition distal surface 82 of the actuating member 80 rests against the proximal end surface of the ledge 114 of the first activator member 110, holding the distal surface of the of the stop ledges 92 of the actuating member the distance "D" from the proximal surface of the annular transversal wall 200 of the distal housing part. During the proximal movement of the plunger, the ledges 74 of the holding member 68 are also moved out of the groove because the arms 78 of the holding member are no longer held in place by the band-shaped part of the actuating mechanism.

The force of the first compression spring urges the plunger to push on the stopper of the syringe 16. But because of the friction between the stopper and the syringe wall and incompressibility of liquid in the syringe and the very small flow passage through the needle, the force will push proximally the syringe and the syringe carrier, and thereby the needle penetrates the skin of the patient. The penetration stops when the proximal surface of the syringe carrier surrounding the neck portion abuts a ledge arranged inside the needle shield. The force from the first compression spring now moves proximally the stopper inside the syringe and the liquid medicament is injected into the patient until the stopper reaches the inner proximal end of the syringe. After the liquid medicament has been injected and the distal end of the plunger rod has passed the ledges 86 of the actuating mechanism, the tongues 90 are radially moved inwards. Because the first compression spring is also acting on the actuating member and has a remaining force, the actuating member is distally moved the distance "D" inside the first activator member, whereby the distal surface of the of the stop ledges 92 of the actuating member strikes against the proximal surface of the annular transversal wall 200 of the distal housing part giving an audible signal to the patient indicating that the delivery e.g. the injection has been completed and that the device can be safely removed from the injection site.

When now the device is removed from the injection site, the force of the needle shield spring pushes proximally the first activator member and thus the needle shield connected to it, whereby the needle shield is proximally pushed out of the front end of the proximal housing part and surrounds the needle.

The movement of the first activator member causes the band-shaped part 84 of the actuating member 80 to pass ribs 111 arranged on the inner surface of the first activator member, FIG. 12b. These ribs prevent any attempts to push the needle shield distally into the device because the ribs will abut the front end of the band-shaped part 84 of the actuating member 80. The needle shield is thus locked, which prevents unintentional needle sticks.

As described above there is required the movement of both the second activator member and thus the actuating member as well as the needle shield and thus the first activator member in order to release the drive mechanism. If the second activator member is depressed but the needle shield is not pressed against an injection site, then the penetration and injection action is not released. Also, if the needle shield is pressed against an injection site but the second activator member is not depressed, then the penetration and injection action is not released.

It is to be understood that the embodiment described above and shown in the drawings is to be regarded as a non-limiting example of the invention, which is defined by the patent claims.

The invention claimed is:

1. An injection device, comprising:
   a generally elongated tubular housing having opposite proximal and distal ends;
   a needle shield sleeve slidably and coaxially arranged inside the housing and protruding a distance outside the proximal end of the housing;
   a syringe carrier mechanism, comprising a syringe carrier slidably and coaxially arranged to the needle shield sleeve, wherein the syringe carrier is configured for a syringe having a medicament and a needle;
   a first activator member slidably and coaxially arranged to the housing and connected to the needle shield sleeve;
   an actuating member slidably and coaxially arranged to the first activator member;

a drive mechanism slidably and coaxially arranged to the actuating member and to the syringe carrier mechanism, wherein the drive mechanism is controlled by the actuating member; and a second activator member slidably and coaxially arranged to the distal end of the housing and fixedly connected to the actuating member;

wherein the first and the second activator members are coaxially movable relative each other from a non-activation position, in which the activator members abut each other, to an activation position, in which the activator members co-act independent of a sequence in which the activator members are activated; and only in the activation position is the actuating member able to release the drive mechanism to move the syringe carrier mechanism for penetrating the needle and delivering the medicament though the needle.

2. The injection device of claim 1, wherein the drive mechanism comprises a plunger rod arranged to act on the syringe and a first compression spring arranged to drive the plunger.

3. The injection device of claim 2, wherein the actuating member comprises flexible tongues having annular inwardly directed ledges, and the plunger rod comprises a circumferential groove having a shape such that the ledges fit into the groove.

4. The injection device of claim 3, wherein the plunger rod is held against a force of the first compression spring by inwardly directed ledges in the groove and by the first activator member, which surrounds and prevents the tongues from moving radially outwards.

5. The injection device of claim 4, wherein the generally elongated tubular housing comprises a distal housing part and a proximal housing part; the distal housing part comprises an annular transversal wall having a through hole having a shape of the distal part of the actuating member, such that the distal part protrudes distally through the through hole until a distal surface of radial outwardly extending stop ledges of the actuating member abuts against a proximal surface of the annular transversal wall.

6. The injection device of claim 5, wherein the distal surface of the radial outwardly extending stop ledges is arranged to strike against the proximal surface of the annular transversal wall for giving an audible signal indicating that medicament delivery has been completed.

7. The injection device of claim 6, further comprising a second compression spring having an annular proximal end resting on a second annular ring of the first activator member and an annular distal end resting on the proximal surface of the stop ledges, such that when the needle shield is removed from an injection site after a medicament delivery, a force of the spring pushes proximally the first activator member and the needle shield, whereby the needle shield is proximally pushed out of the front end of the proximal housing part to surround the needle.

8. The injection device of claim 7, wherein the first activator member comprises ribs on its inner surface arranged to interact with a band-shaped part of the actuating member when the spring pushes proximally the first activator member and the needle shield, for preventing pushing the needle shield distally into the device.

* * * * *